US010422707B2

(12) United States Patent
Bradford

(10) Patent No.: US 10,422,707 B2
(45) Date of Patent: *Sep. 24, 2019

(54) COMPACT ROBOTIC FORCE/TORQUE SENSOR INCLUDING STRAIN GAGES

(71) Applicant: ATI Industrial Automation, Inc., Apex, NC (US)

(72) Inventor: Everett Lester Bradford, Apex, NC (US)

(73) Assignee: ATI Industrial Automation, Inc., Apex, NC (US)

(*) Notice: Subject to any disclaimer, the term of this patent is extended or adjusted under 35 U.S.C. 154(b) by 566 days.

This patent is subject to a terminal disclaimer.

(21) Appl. No.: 15/000,260

(22) Filed: Jan. 19, 2016

(65) Prior Publication Data

US 2017/0205296 A1    Jul. 20, 2017

(51) Int. Cl.
*G01L 1/22* (2006.01)
*G01L 3/10* (2006.01)
(Continued)

(52) U.S. Cl.
CPC ............. *G01L 1/22* (2013.01); *B25J 13/085* (2013.01); *G01L 1/2206* (2013.01); *G01L 3/108* (2013.01); *G01L 5/161* (2013.01); *G01N 3/08* (2013.01)

(58) Field of Classification Search
CPC . G01L 5/161; G01L 3/24; G01L 3/108; G01L 1/22; G01L 1/2206; G01B 7/18; G01B 5/30; B25J 13/085; G01N 3/08
See application file for complete search history.

(56) References Cited

U.S. PATENT DOCUMENTS 4,969,366 A * 11/1990 Okada ...................... G01L 1/18
                                                            73/777
5,969,268 A * 10/1999 Sommerfeld ......... G01L 1/2206
                                                        73/862.041
(Continued)

FOREIGN PATENT DOCUMENTS

JP        S54125088 A    9/1979
JP        S6259826 A     3/1987
(Continued)

*Primary Examiner* — Harshad R Patel
*Assistant Examiner* — Nigel H Plumb
(74) *Attorney, Agent, or Firm* — Coats & Bennett PLLC

(57) ABSTRACT

A force/torque sensor comprising a Tool Adapter Plate (TAP) connected to a Mounting Adapter Plate (TAP) by one or more radially-spaced, deformable beams features a pair of strain gages affixed to only one surface of each beam. The two strain gages are affixed to, e.g., the top surface on either side of, and spaced away from, a neutral axis of the beam. This enables a very compact sensor design, in one embodiment, machined from a single piece of metal stock. The two sensors may be connected in a quarter bridge topology. In one embodiment, another pair of strain gages is affixed to the same side of the beam, and the four gages are wired in a half-bridge topology. In another embodiment, a second pair of strain gages is affixed to the opposite side of the beam, and the four gages are wired in a half-bridge topology—although this embodiment gives up some of the space and ease of manufacture advantages, it allows for electrical elimination of common-mode signal components, such as those induced by temperature drift. In one embodiment, a strain gage is connected to a non-stressed member of the sensor 10 to provide a signal for temperature calibration.

14 Claims, 10 Drawing Sheets

(51) Int. Cl.
*G01N 3/08* (2006.01)
*B25J 13/08* (2006.01)
*G01L 5/16* (2006.01)

(56) References Cited

U.S. PATENT DOCUMENTS

| | | | |
|---|---|---|---|
| 6,951,142 B2* | 10/2005 | Ohsato | G01L 5/162 |
| | | | 73/862.041 |
| 7,252,453 B1* | 8/2007 | Little | B25J 15/04 |
| | | | 403/322.2 |
| 7,703,340 B2 | 4/2010 | Sakurai et al. | |
| 8,250,934 B2 | 8/2012 | Sakurai | |
| 2005/0120809 A1* | 6/2005 | Ramming | G01L 5/161 |
| | | | 73/862.044 |
| 2015/0033875 A1* | 2/2015 | Meyer | G01L 5/168 |
| | | | 73/862.041 |
| 2015/0135856 A1 | 5/2015 | Kim et al. | |
| 2017/0211999 A1* | 7/2017 | Bradford | B25J 13/085 |

FOREIGN PATENT DOCUMENTS

| | | |
|---|---|---|
| JP | S63266329 A | 11/1988 |
| JP | H03216529 A | 9/1991 |
| JP | H11304606 A | 11/1999 |
| JP | 2008058110 A | 3/2008 |
| JP | 2010185725 A | 8/2010 |
| WO | 9904235 A1 | 1/1999 |

* cited by examiner

COMPACT ROBOTIC FORCE/TORQUE SENSOR INCLUDING STRAIN GAGES

FIELD OF INVENTION

The present invention relates generally to a force/torque sensor for robotic applications, and in particular to a compact force/torque sensor featuring strain gages affixed to only one surface of a deformable beam.

BACKGROUND

Robotics is a growing, and increasingly important, field in industrial, medical, scientific, and other applications. In many cases, in which a robot arm or a tool attached thereto contacts a workpiece, the force and/or torque applied must be closely monitored. Accordingly, a force/torque sensor is an important part of many robotic systems.

One conventional type of force/torque sensor uses strain gages to measure the deformation of small beams connecting two mechanical parts—one connected to the robot arm and the other connected to a robotic tool (or a mechanical coupling to the tool). For example, a central "hub," referred to in the art as a Tool Adapter Plate (TAP) is connected to a tool. Another body arranged annularly around, and spaced apart from, the TAP, referred to in the art as a Mounting Adapter Plate (MAP), is connected to a robotic arm. The MAP and TAP are connected to each other by a plurality of relatively thin (and hence mechanically deformable) beams, arranged radially around the TAP—in some cases resembling spokes of a wheel. Relative force or torque between objects respectively attached to the TAP and MAP attempt to move the MAP relative to the TAP, resulting in slight deformation, or bending, of at least some of the beams.

Conventionally, strain gages are affixed to all four surfaces of each beam, nominally in the center of each respective surface. The gages translate tensile and compressive strains at the beams' surfaces into electrical signals. As an example of their operation, consider forces in or parallel to the plane of the TAP and MAP—i.e., a z-direction torque (Tz, using the "right-hand rule") or an x- or y-direction force (Fxy). These forces will attempt to bend at least some of the beams to the side. In this case, a strain gage on one side of a beam will detect a compressive strain, and a gage on the opposite side of the beam will detect a tensile strain. These gages will output strong signals, of opposite polarity. Strain gages on the top and bottom surfaces of the same beam will output very weak, if any, signals. Conversely, forces attempting to move the MAP or TAP out of their common plane (Fz, Txy) will generate strong, and opposite, outputs from the strain gages on the top and bottom beam surfaces, with little contribution from strain gages on the sides. Once calibrated, signals from all four strain gages on all beams are processed together to resolve the magnitude and direction of relative force and/or torque between the robot arm and tool (and hence the force/torque applied through the tool to a workpiece).

Instrumentation of a force/torque sensor is a significant source of cost in the product, as it requires precise and highly-skilled manual labor. Instrumentation also imposes design constraints on the sensor's mechanical design, because a significant amount of physical space is required around each of the four instrumented surfaces of each beam for viewing and hand tool access. These constraints become particularly restrictive at very small sensor sizes, and can necessitate sub-optimal sensor geometry to accommodate the installation and inspection of instrumentation. Furthermore, lengthy and complex bond wire routing is required to transfer electrical signals from strain gages on all four surfaces of each beam to a central processing circuit, which may increase the risk of device failure.

The Background section of this document is provided to place embodiments of the present invention in technological and operational context, to assist those of skill in the art in understanding their scope and utility. Unless explicitly identified as such, no statement herein is admitted to be prior art merely by its inclusion in the Background section.

SUMMARY

The following presents a simplified summary of the disclosure in order to provide a basic understanding to those of skill in the art. This summary is not an extensive overview of the disclosure and is not intended to identify key/critical elements of embodiments of the invention or to delineate the scope of the invention. The sole purpose of this summary is to present some concepts disclosed herein in a simplified form as a prelude to the more detailed description that is presented later.

According to one or more embodiments described and claimed herein, a force/torque sensor comprises a pair of strain gages affixed to only one surface of each beam connecting a TAP and MAP. The two strain gages are affixed to, e.g., the upper surface on either side of, and spaced away from, a neutral axis of the beam. By only requiring access to the upper beam surface, a very compact sensor design is possible—in one embodiment, machined from a single piece of metal stock. The single surface enables the use of automated manufacturing technologies, such as wire bonding the strain gages to pads of a circuit board, or surface-mounting the strain gages to a flexible circuit substrate and adhering the substrate to the beam surface. The two strain gages may be connected in a quarter bridge topology. In a three-beam, six-gage configuration, the positive and negative outputs of the six strain gages (due to transducing either compressive or tensile forces) sum to zero in five of the six force/torque axes (Fx, Fy, Fz, Tx, Ty, Tz); prior art force/torque sensor designs achieve this for only four of six axes. This facilitates mathematical cancellation of common-mode signal components, such as temperature drift. In one embodiment, another pair of strain gages is affixed to the same side of the beam, and the four gages are wired in a half-bridge topology. In another embodiment, a second pair of strain gages is affixed to the opposite side of the beam, and the four gages are wired in a half-bridge topology. The half bridge topologies achieve electrical elimination of common-mode signal components. In one embodiment, which one of the six axes that does not sum to zero may be selected by inverting the excitation potential. In one embodiment, a seventh strain gage is connected to a non-stressed member of the sensor to provide a signal for temperature calibration.

One embodiment relates to a force/torque sensor. The sensor includes a Tool Adapter Plate (TAP) operative to be connected to a first object, and a Mounting Adapter Plate (MAP) operative to be connected to a second object. The sensor also includes one or more deformable beams connecting the TAP to the MAP. A first pair of strain gages is affixed to only one side of each beam. The strain gages are on opposite sides of, and spaced apart from, a neutral axis of the beam, and they are operative to transduce tensile and compressive forces on the surface of the one side of the beam, caused by deformation of the beam, into electrical signals. The sensor further includes a measurement circuit operative to measure, in response to electrical signals from all strain gages, the direction and magnitude of force and torque between the first and second objects.

Another embodiment relates to a method of fabricating a single-piece force/torque sensor from a disc-shaped metal stock. The stock has coplanar top and bottom surfaces of a generally circular shape, with a thickness between the top and bottom surface. Blind pockets are milled into and transverse to the top surface. The blind pockets extend in depth less than the thickness of the stock. The blind pockets define a generally circular hub in the center of the stock, an annular body surrounding the hub, and one or more beams disposed radially around the hub and connecting between the hub and the annular body. The top surfaces of the hub and beams are milled down to be lower than the top surface of the annular body. A relief cut is milled parallel to the top surface, at a distance from the top surface no greater than the depth of the blind pockets. The relief cut is milled through the annular body and beams, but not through the hub. The relief cut defines a floor to which the hub is connected, but the annular body and beams are not, thus leaving the annular body connected to the hub only by the beams. A pair of strain gages is affixed to only the top side of each beam, on opposite sides of, and spaced apart from, a neutral axis of the beam. The strain gages are operative to transduce tensile and compressive forces on the surface of the top side of the beam, which are caused by deformation of the beam, into electrical signals. The strain gages on each beam are electrically connected to a processing circuit.

BRIEF DESCRIPTION OF THE DRAWINGS

The present invention will now be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. Like numbers refer to like elements throughout.

DETAILED DESCRIPTION

For simplicity and illustrative purposes, the present invention is described by referring mainly to an exemplary embodiment thereof. In the following description, numerous specific details are set forth in order to provide a thorough understanding of the present invention. However, it will be readily apparent to one of ordinary skill in the art that the present invention may be practiced without limitation to these specific details. In this description, well known methods and structures have not been described in detail so as not to unnecessarily obscure the present invention.

Inventive Strain Gage Placement

Figure 1:
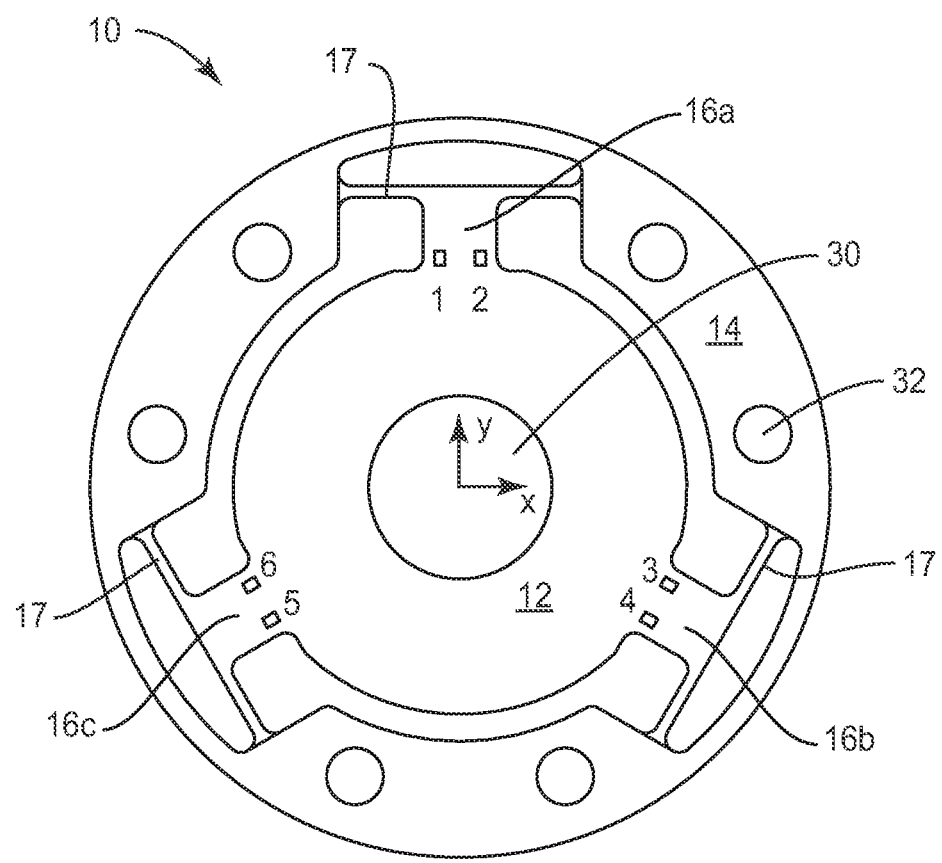
FIG. 1 is a plan view of a force/torque sensor.

FIG. 1 depicts a plan view of one embodiment of a force/torque sensor 10 according to one embodiment of the present invention. A TAP 12 is connected to a MAP 14 by three beams 16a, 16b, 16c. In the embodiment depicted, each beam 16 connects directly to the TAP 12, and connects to the MAP 14 by flexures 17, which aid in the deformation of the beams 16 under mechanical loading. The TAP 12 is configured to be connected to a first object, such as a robotic tool, via a through-hole 30 or by tapped holes in the underside of the sensor 10 (not shown in FIG. 1). The MAP 14 is configured to be connected to a second object, such as a robot arm, via a plurality of mounting holes 32. Although not clear from this view, the TAP 12 and MAP 14 are only connected by the beams 16.

Affixed to (only) the upper surface of each beam 16 are strain gages 1-6. As a reference for later discussion, gages 1 and 2 are affixed to beam 16a; gages 3 and 4 are affixed to beam 16b, and gages 5 and 6 are affixed to beam 16c. FIG. 1 also depicts two axes of a 3-dimensional reference Cartesian coordinate system (z-direction extending out of the figure), which will be used to unambiguously label forces and torques in the ensuing disclosure. Although not depicted in FIG. 1, the force/torque sensor 10 also includes a processing circuit operative to receive electrical signals from each strain gage 1-6, and to process the signals to resolve the magnitude and direction of force(s) and torque(s) applied between the MAP 14 and TAP 12. Such processing circuits may comprise, e.g., a microprocessor coupled to memory operative to store program code and sensor data.

Figure 2:
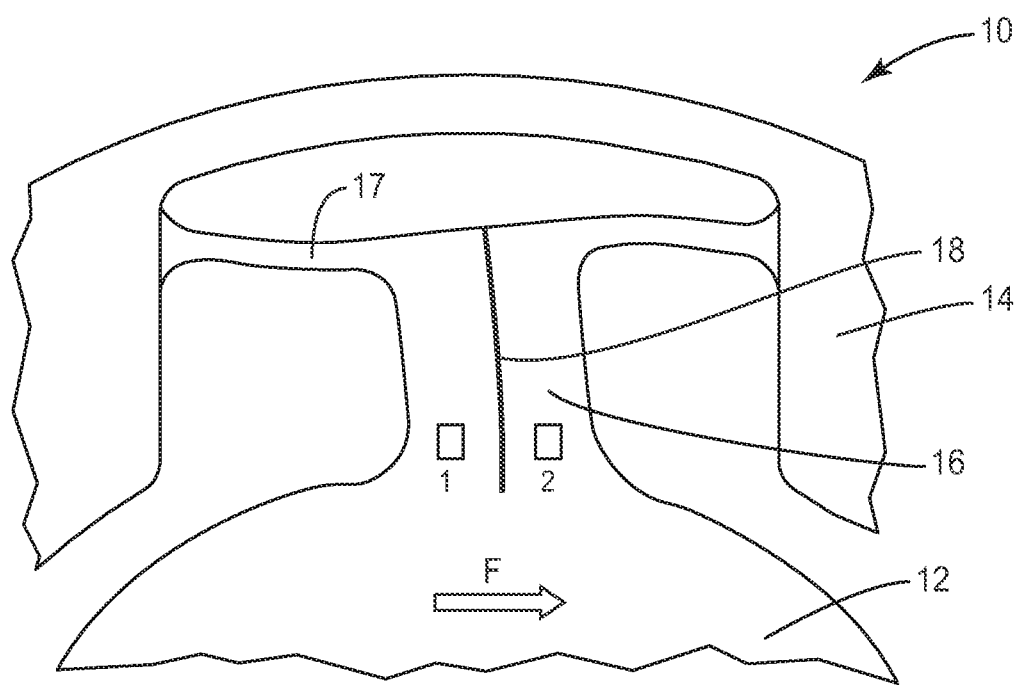
FIG. 2 is an enlarged view of one beam of the force/torque sensor of FIG. 1.

FIG. 2 is an enlarged view of one beam 16a undergoing deformation due to a force F applied to the TAP 12, relative to the MAP 14. This force deforms the beam 16a slightly to the left (the figure is not to scale). A compressive force is induced on the left side surface of beam 16a, and a tensile force is induced on the right side surface. In the prior art, strain gages mounted on these surfaces would generate strong signals, of opposite polarity, from which the deformation, and hence the applied force F, could be ascertained. However, the two sides of the upper surface of the beam 16a also experience the compressive and tensile strain, in a magnitude that increases with distance away from a neutral axis 18. The neutral axis 18 is the line, running generally down the center of the upper surface of the beam 16a, at which compressive strain experienced on the left side of the beam 16a transitions to tensile strain on the right side. Accordingly, the beam 16a undergoes no strain at the neutral axis 18.

According to embodiments of the present invention, a pair of strain gages 1, 2 is affixed to only the upper surface of beam 16a. The strain gages 1, 2 are located to either side of, and spaced apart from, the neutral axis 18. Differential signals, such as signals having opposite polarities, from the strain gages 1, 2 indicate bending of the beam 16a in the plane of the upper surface (i.e., Tz, Fxy). Common-mode signals (same polarity) would indicate bending of the beam 16a in the z-direction (i.e., caused by Fz, Txy).

Figure 3:
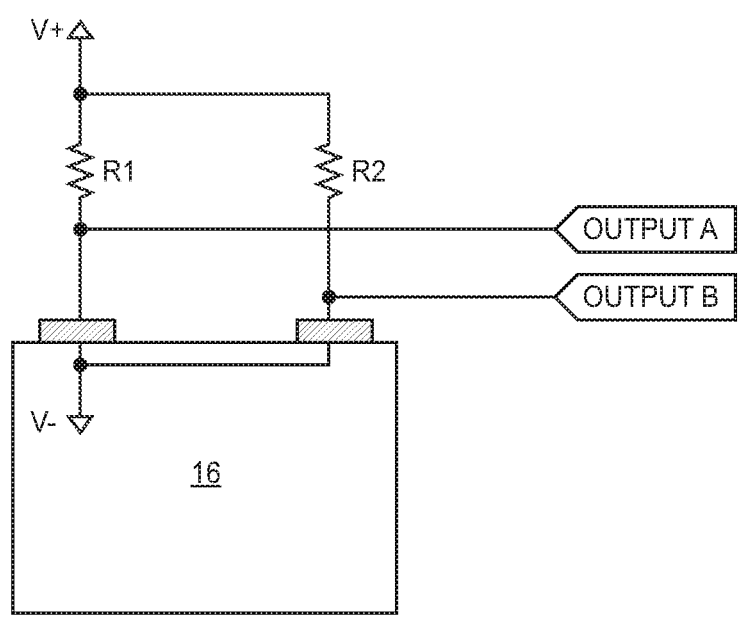
FIG. 3 is a section view and functional circuit schematic of a quarter bridge circuit topology of strain gages on a beam.

In one embodiment, the pair of strain gages on each beam 16 is wired in a quarter bridge topology, using two fixed resistors, as depicted in FIG. 3. The six strain gages 1-6, affixed to beams 16a-c as depicted in FIG. 1, generate the following signals under the six applied forces and torques, using the reference Cartesian coordinate system of FIG. 1. In the following table, a strong tensile force is denoted by "T," a weak tensile force by "t," a strong compressive force by "C," and a weak compressive force by "c."

TABLE 1

Strain Gage Outputs under Specific Forces/Torques

| | Force X | Force Y | Force Z | Torque X | Torque Y | Torque Z |
|---|---|---|---|---|---|---|
| Gage 1 | C | none | T | T | none | T |
| Gage 2 | T | none | T | T | none | C |
| Gage 3 | t | T | T | c | C | T |
| Gage 4 | c | C | T | C | C | C |
| Gage 5 | t | C | T | C | T | T |
| Gage 6 | c | T | T | c | T | C |

It is clear by inspection of Table 1 that the signals generated under each loading condition follow unique patterns, and can therefore be resolved into forces and torques by a known calibration matrix process.

Single-Piece Sensor Fabrication and Automated Wring Options

The need for access to only one beam surface creates significant advantages in manufacturing the mechanical parts of a force/torque sensor. In one embodiment, an entire sensor is manufactured from a single piece of metal. This eliminates the conventional, separate MAP and TAP pieces, and the mechanical interfaces to them, thus reducing parts count and required assembly steps. Additionally, the single-piece design is more compact than prior art force/torque sensors operative over the same range of force/torque magnitudes, due to the need for access to only the upper surface of the beams 16 to mount the strain gages 1-6. Furthermore, the single-piece design has very high stiffness, and zero chance of slippage, as there are no bolted joints.

Figure 4A:
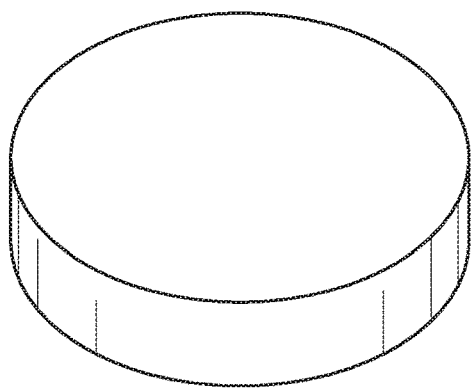
FIGS. 4A-4G are perspective views depicting successive steps in the manufacture of single-piece force/torque sensor.
Figure 4B:
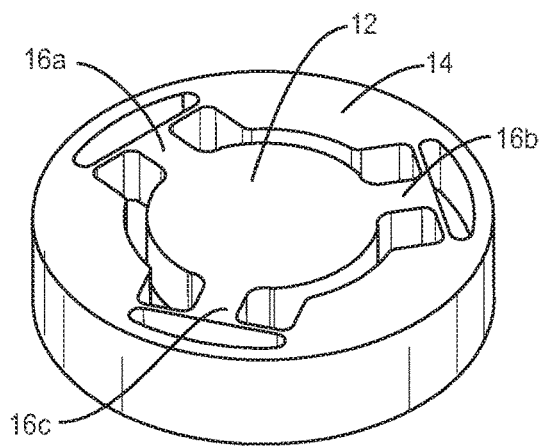
Figure 4C:
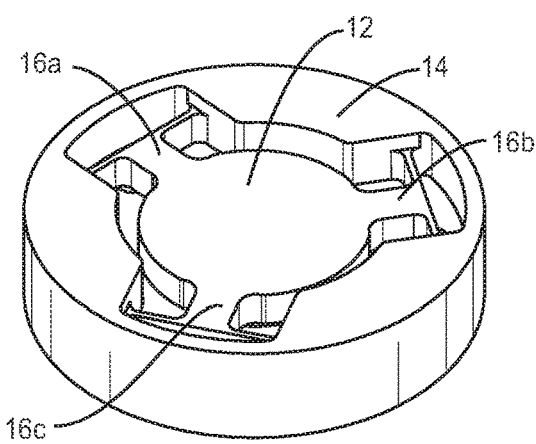
Figure 4D:
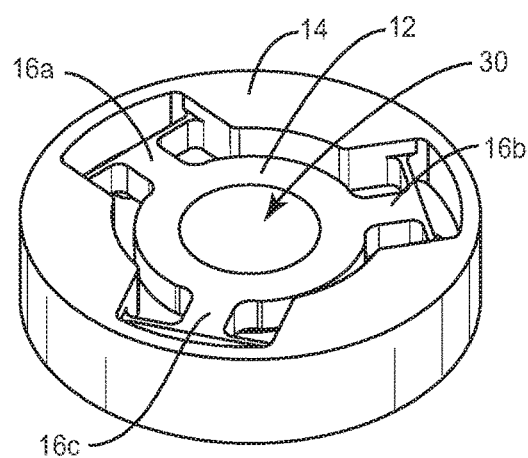
Figure 4E:
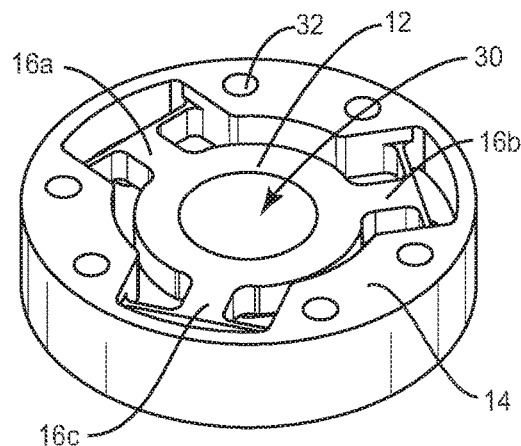
Figure 4F:
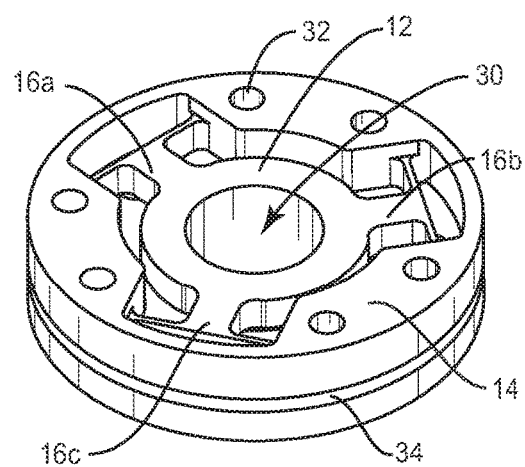
Figure 4G:
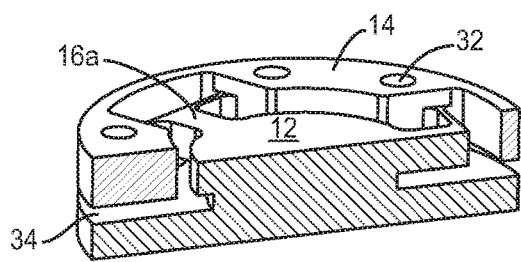

A single-piece force/torque sensor fabricated from, e.g., aluminum, is presented in FIGS. 4F and 4G. The sensor 10 includes a through hole 30 through the TAP 12 portion and mounting features 32 on the MAP 14 portion. It can be manufactured without electrical discharge machining (EDM), using endmill cutting tools no smaller than 3/32nd inches, according to a method depicted with reference to FIGS. 4A-G.

FIG. 4A depicts the starting point: a disc-shaped piece of metal stock, having parallel, generally circular top and bottom surfaces, and a thickness between them. As depicted in FIG. 4B, blind pockets are milled to form the beams 16 and flexures 17, which also begin to form a hub, which will become the TAP 12, as being separate from an annular body, which will become the MAP 14.

FIG. 4C shows that the upper surface of the TAP 12, beams 16, and flexures 17 are milled down, below the upper surface of the MAP 14. This creates a raised mounting surface for the MAP 14 side of the sensor 10. A non-structural cover can be installed later to protect the beams 16 and electronics from dust and mechanical damage. If a through hole 30 is desired for mounting, or for the passage of electrical or fluid lines, it is drilled through TAP 12, as depicted in FIG. 4D.

FIG. 4E depicts the MAP 14 mounting holes 32 drilled and tapped. In one embodiment, for additional cost reduction, the mounting holes 32 have an identical pattern on the MAP and TAP sides and are drilled and tapped through in a single step.

Next, a relief cut 34 is made in the side of the sensor 10, as shown in FIG. 4F. The relief cut 34 is no lower (as measured from the top surface of MAP 14) than the depth of the blind pockets milled out to form the beams 16 and flexures 17. Accordingly, the relief cut 34 separates the MAP 14 from any mechanical connection to the TAP 12, other than via the beams 16. In other words, and as best depicted in the section view of FIG. 4G, while the TAP 12 is connected to the "floor" of the sensor below the relief cut 34, the MAP 14 is not—rather, it "floats" free of the sensor 10, connected to the TAP 12 only by the beams 16 and flexures 17. In the finished product, the gap 34 may be filled with a compressible foam gasket to prevent dust ingress.

FIG. 4F shows the finished force/torque sensor 10 body in full perspective view, and FIG. 4G shows the finished sensor body in sectional perspective view. In various embodiments, additional features may be included protect the electronics, to provide wiring and LED indicator access, and the like. In one embodiment, a section of the TAP 12 is milled to largely remove all mechanical strain from it, forming a mounting location for a temperature compensating gage, which is discussed more fully herein.

Figure 5:
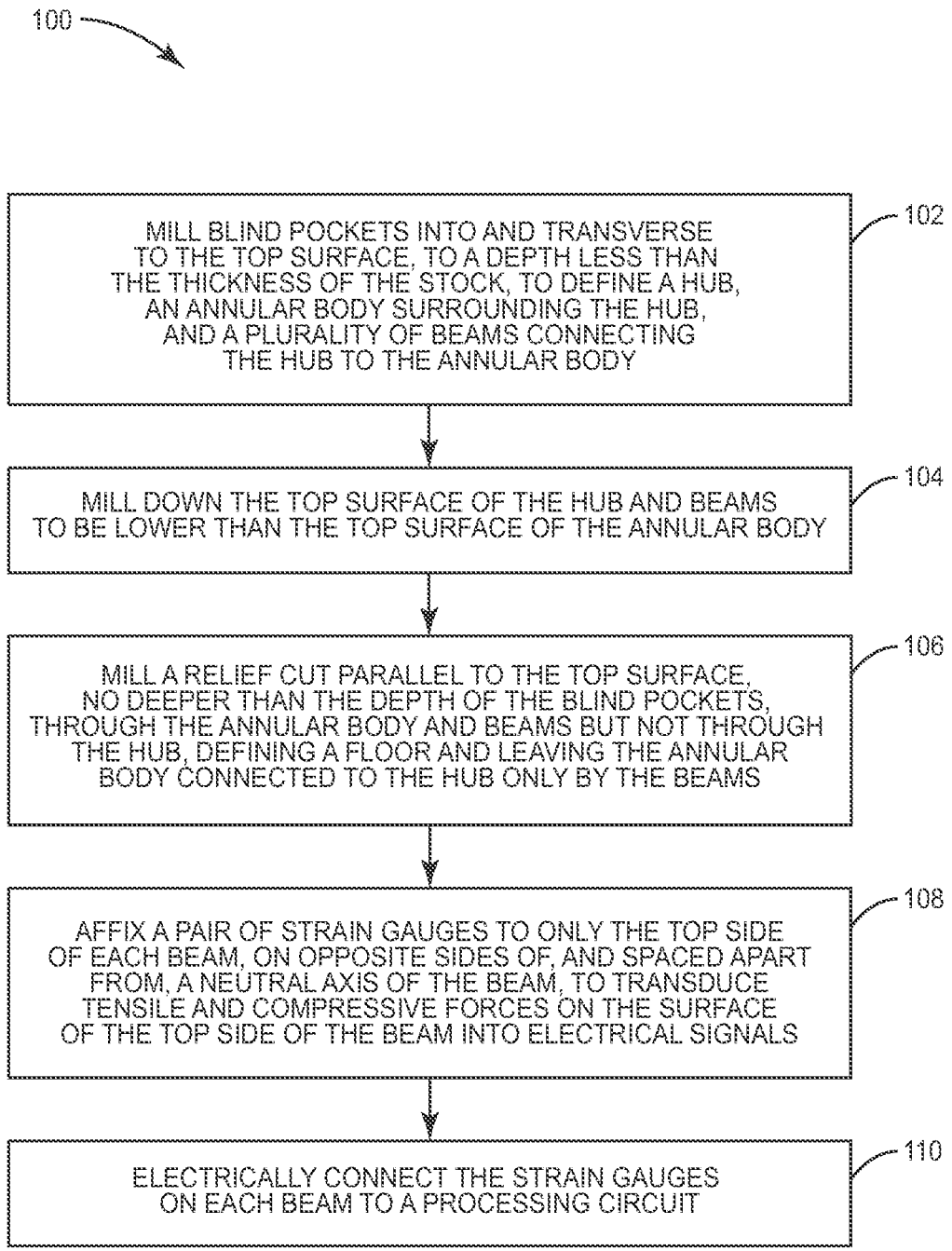
FIG. 5 is a flow diagram of a method of fabricating a single-piece force/torque sensor.

FIG. 5 depicts the steps of a method 100 of fabricating a single-piece force/torque sensor 10 from a disc-shaped metal stock. The stock has coplanar top and bottom surfaces of a generally circular shape, and a thickness between the top and bottom surface. First, blind pockets are milled into and transverse to the top surface. The blind pockets extend in depth less than the thickness of the stock. They define a generally circular hub 12 in the center of the sensor, an annular body 14 surrounding the hub, and a plurality of beams 16 disposed radially around the hub 12 and connecting between the hub 12 and the annular body 14 (block 102). The top surfaces of the hub 12 and beams 16 are milled down to be lower than the top surface of the annular body 14 (block 104).

A relief cut 34 is milled parallel to the top surface, at a distance from the top surface no greater than the depth of the blind pockets. The relief cut 34 extends through the annular body 14 and beams 16, but not through the hub 12. The relief cut 34 defines a floor to which the hub 12 is connected, but the annular body 14 and beams 16 are not. This leaves the annular body 14 connected to the hub 12 only by the beams 16 (block 106).

A pair of strain gages 1-6 is affixed to only the top side of each beam 16. The two strain gages 1-6 on each beam 16 are placed on opposite sides of, and spaced apart from, a neutral axis 18 of the beam 16. The strain gages 1-6 are operative to transduce tensile and compressive forces on the surface of the top side of the beam 16, which are caused by deformation of the beam 16, into electrical signals (block 108). The strain gages 1-6 on each beam 16 are electrically connected to a processing circuit (block 110).

In one embodiment, the blind pockets further define flexures 17 transverse to each beam 16, disposed at the distal end of the beam 16 from the hub 12. The flexures 17 connect to the annular body 14. As additional steps, a through hole 30 may be drilled through the hub 12, for mounting to a tool, or to facilitate the passage of electrical wires or fluid lines; and a plurality of mounting holes 32 may be drilled and tapped in the annular body 14, for mounting to a robotic arm. Additional features may be formed, such as passageways for wiring and LEDs, and a non-stressed member 37 (see FIG. 8) for the mounting of a temperature compensating strain gage.

The force/torque sensor 10 of FIGS. 4A-G is more compact, and requires the fabrication and assembly of fewer parts, than prior art force/torque sensors. Locating the strain gages 1-6 on only the top surface of the beams 16 also enables shorter wire runs, easy sightlines and hand tool access, and fewer geometry constraints than the prior art. Furthermore, the inventive placement of all strain gages 1-6 on the top surfaces of beams 16 enables additional cost-saving manufacturing options.

Figure 6:
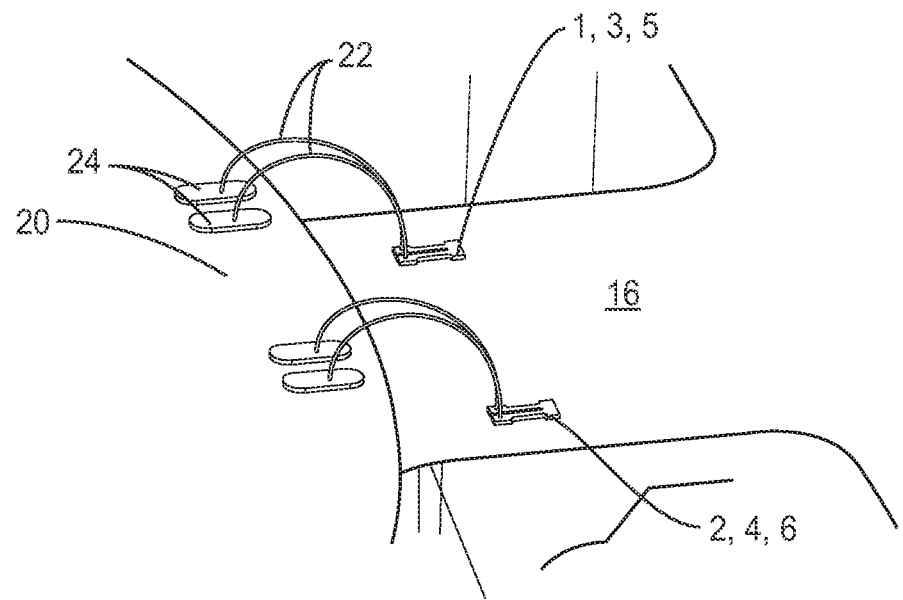
FIG. 6 is a perspective view of wirebonding strain gages to a PCB.

In one embodiment, depicted in FIG. 6, gages 1-6 without bond wires are attached to the beams 16 by conventional means (e.g., manually, with epoxy). A printed circuit board (PCB) 20 with wirepads 24 is adhered to the surface of the TAP 12. Electrical connections 22 are then formed directly between the gages 1-6 and the PCB wirepads 24 with a wirebonding machine, eliminating all manual handling of bond wires. As well known in the electronic arts, automated wirebonding is faster, more accurate, and cheaper than manual wiring.

Figure 7:
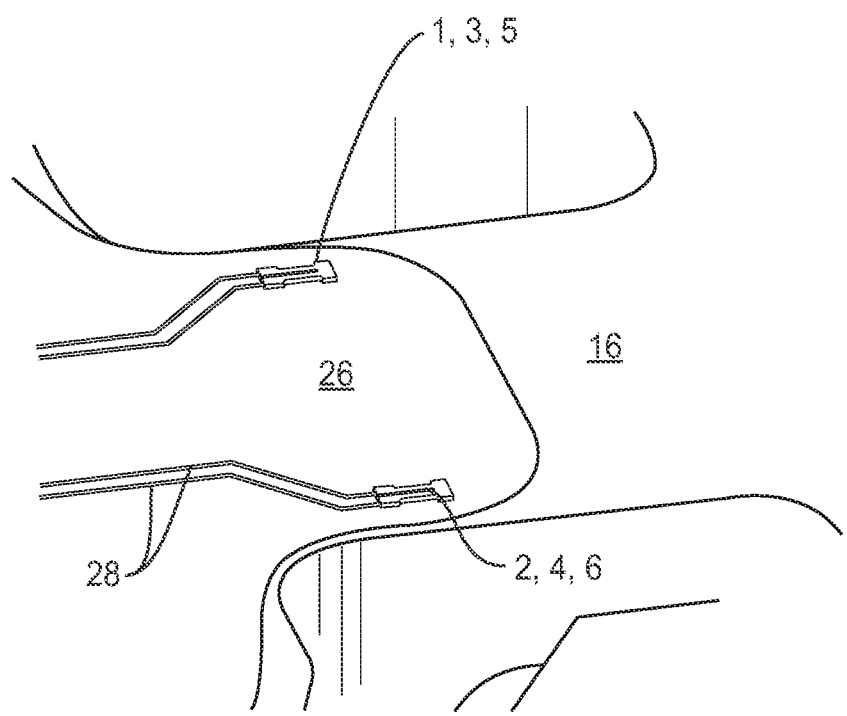
FIG. 7 is a perspective view of strain gages surface-mounted to a flexible circuit substrate.

In another embodiment, as depicted in FIG. 7, gages 1-6 are mounted, with solder pads, face down onto surface mount device (SMD) pads on a flexible circuit substrate 26, such as polyimide film. The flexible substrate 26 is adhered to the sensor 10 body, such as over the TAP 12, and has tabs that extend at least partially onto the top surface of each beam 16. The gages 1-6 are populated on the flexible substrate 26, along with all other circuit components, by a pick-and-place machine and reflowed to solder them down. The SMD pads are connected to other electronics by preformed circuit traces 28, e.g., copper, on the substrate 26. This eliminates all gage wiring, at the cost of reduced signal magnitude (e.g., lower signal to noise ratio) due to flexing in the polyimide material. In this embodiment, both manual attachment and wiring of the strain gages 1-6 are eliminated, achieving cost reduction and increased quality, uniformity, and production speed.

Zero-Sum Coefficients

In prior art, 3-beam force/torque sensors, there are two sets of three half-bridge topologies of strain gages—the top/bottom and the left/right gages affixed to each beam. Each of these sets is largely separate from the other in terms of the external loads to which they respond—the left/right set responds to horizontal beam bending (induced by Tz and Fxy) while the top/bottom set responds to vertical bending (induced by Txy and Fz). In this arrangement, when Fxy or Txy are applied, some beams bend in one direction while other beams bend in the opposite direction, generating signals of opposite polarity on the respective gage pairs. Because of this behavior, coefficients in a calibration matrix have differing polarities for the various gage pairs in the equation, which resolves an X/Y load. In an ideal transducer (without significant gage misalignment or crosstalk), the coefficients for these X/Y equations will sum to nearly zero because the various gage pairs are contributing equally to the calculated output, but are being strained in opposite directions. When the coefficients sum to zero in this way, any common-mode signals appearing on the gages are canceled mathematically. These common-mode signals are generally temperature-induced effects which should be rejected by the system in calculating its final outputs.

Because the traditional gauging arrangement has two cases in which the three active gages respond in the same way (Fz and Tz), these two axes cannot sum to zero and will therefore exhibit poorer performance during warmup (drift) and other changes in temperature as the unwanted common-mode signals from all gages are compounded instead of cancelled.

In contrast, embodiments of the present invention present the significant advantage that because all (top-surface only) gages respond to all types of loading, they present a zero sum also for the Tz axis, while retaining the zero-sum advantage on X/Y loading cases as in the prior art. This is because under Tz in the inventive sensor 10, there are six active signals of equal magnitude: three with positive polarity and three with negative polarity. Fz is the only axis which does not sum to zero, and an alternate compensation method must be used in this one case to achieve performance on par with the other five axes. Table 2 below exhibits this performance feature, for the configuration depicted in FIG. 1, with the circuit topology depicted in FIG. 3:

TABLE 2

| Gage Output Polarity under Specific Forces/Torques | | | | | | | |
|---|---|---|---|---|---|---|---|
| Beam | 16a | | 16b | | 16c | | |
| Gage | 1 | 2 | 3 | 4 | 5 | 6 | Sum |
| Force x | − | + | + | − | + | − | 0 |
| y | | | + | − | − | + | 0 |
| z | + | + | + | + | + | + | 6+ |
| Torque x | + | + | − | − | − | − | 0 |
| y | | | − | − | + | + | 0 |
| z | + | − | + | − | + | − | 0 |

Each row sums to zero, with the exception of Fz (third row), in which case all gages output a positive polarity signal.

Temperature Compensation

The most simple and least expensive implementation of the top-surface only gages is to employ a quarter bridge circuit topology. Quarter bridge topology has certain inherent disadvantages over the traditional half bridge topology employed when two gages are present, the most prominent of which is temperature-induced error. In a half bridge topology, signals that affect each gage equally (usually induced by temperature changes) will be canceled by their electrical arrangement, and only differential signals (induced by the extension of one gage and the compression of the other) will be present at the half bridge circuit output.

Figure 8:
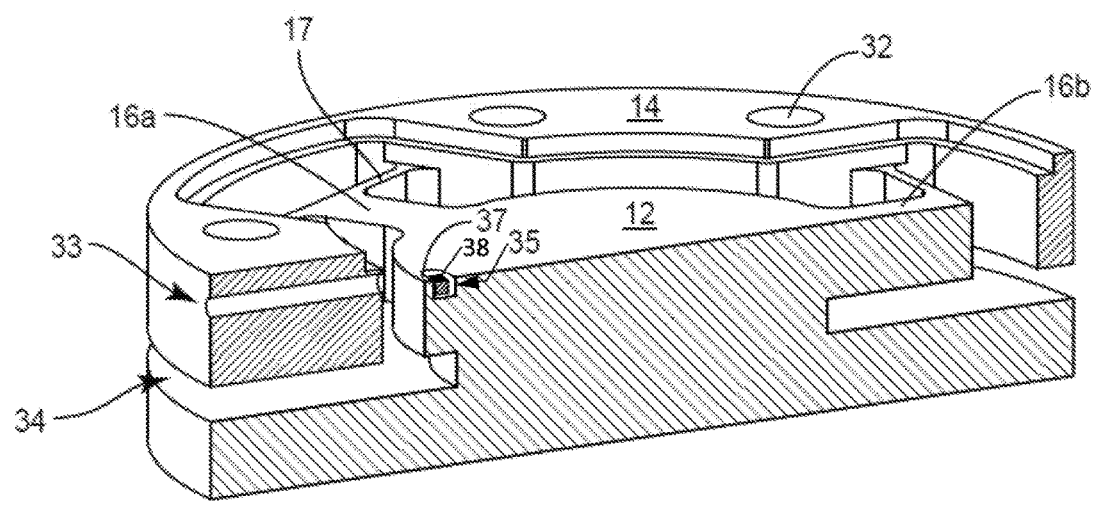
FIG. 8 is a perspective section view of a force/torque sensor showing a non-stressed member for mounting a temperature compensating strain gage.

According to some embodiments of the present invention, in order to mitigate this issue in a quarter bridge topology, a temperature compensation method is used. In one embodiment, a seventh strain gage 38, which is identical to the six active gages 1-6, is affixed to a part of the force/torque sensor 10 that will not experience any mechanical strain under an applied force or torque. The signal from a seventh strain gage 38 mounted on this extension 37, which is affected by temperature only and not loading, is then removed mathematically from the signals from the other six gages 1-6 when calculating the resolved loads, to compensate for temperature drift. As depicted in FIG. 8, in order to achieve the smallest possible amount of mechanical coupling to the seventh gage 38, an area 35 of the force/torque sensor 10 is milled away to define a thin, cantilevered extension 37 which does not carry any mechanical strain. The temperature-compensating strain gage 38 is mounted to the end of the extension 37. FIG. 8 additionally shows that other features may be milled out as required or desired, such as wiring channel 33.

Half Bridge Topologies

Figure 9:
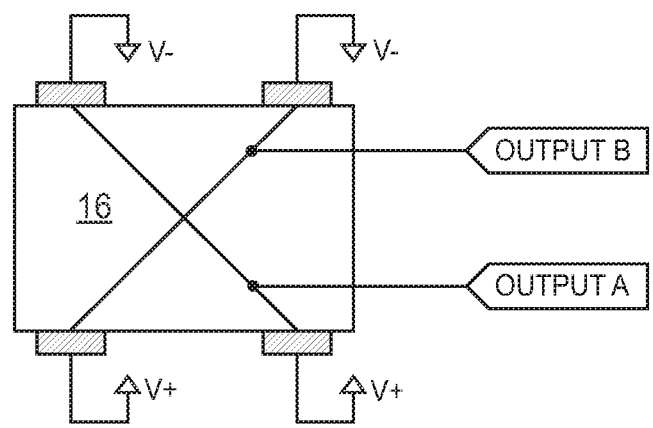
FIG. 9 is a section view and functional circuit schematic of an X connection half bridge circuit topology of strain gages on a beam.

In other embodiments of the present invention, both the temperature-cancelling advantages of half bridge circuit topology and the zero sum advantage on five of six force/torque axes are achieved by replicating the placement of two strain gages on the bottom surface of each beam 16, as well as the top surface. The four gages on each beam 16 are then connected in an X configuration to achieve a half bridge circuit topology, as depicted in FIG. 9. This configuration generates the same output pattern as the quarter bridge topology, as depicted in Table 2 above.

In affixing pairs of strain gages to both the top and bottom surfaces of each beam 16, some of the inherent space and cost advantages of the top-surface only embodiments are forfeit—for example, a sensor 10 design must allow access to the bottom surfaces of beams 16 to allow for instrumentation and wire routing. However, in applications where temperature drift elimination is more important than sensor 10 size or manufacturing cost, these embodiments retain significant advantages over the prior art. For example, the gage outputs still sum to zero in five of six force/torque axes (true for only four of six in the prior art), and the sensor 10 design may still be more compact in that access to the side surfaces of the beams 16 is not required.

Figure 10:
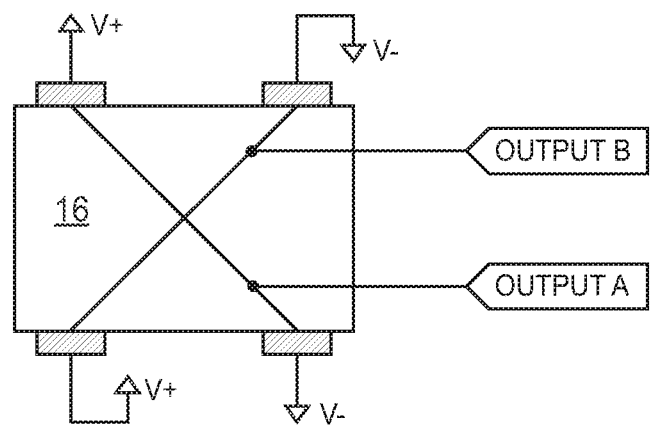
FIG. 10 is a section view and functional circuit schematic of a half bridge circuit topology having an inverted excitation polarity.

In one half bridge topology embodiment, the excitation polarity of one of the strain gages is inverted, as depicted in FIG. 10. This has the effect of moving the non-zero-sum axis from Fz to Tz, as indicated by Table 3 below:

TABLE 3

Half Bridge Gage Output Polarity with Inverted Excitation Polarity

| Beam | | 16a | | 16b | | 16c | |
| --- | --- | --- | --- | --- | --- | --- | --- |
| Gage | 1 | 2 | 3 | 4 | 5 | 6 | Sum |
| Force x | + | + | − | − | − | − | 0 |
| y | | | − | − | + | + | 0 |
| z | − | + | − | + | − | + | 0 |
| Torque x | − | + | + | − | + | − | 0 |
| y | | | − | + | + | − | 0 |
| z | − | − | − | − | − | − | 6− |

This embodiment finds particular utility in applications where Tz does not occur, or is otherwise of lesser importance than accurate measurement of Fz.

In another embodiment, where the applied forces/torques are applied for a duration that is longer than merely instantaneous, a switching circuit first applies the excitation polarity of FIG. 9, and obtains zero-sum signals for all axes other than Fz. The applied excitation voltage is then switched to the configuration depicted in FIG. 10, and a zero-sum reading is obtained for Fz, while Tz generates the non-zero-sum signals. In this manner, zero-sum equations are applied to all six force/torque axes, and all common-mode signals, such as temperature-induced errors, are eliminated. This eliminates the need for a dedicated temperature compensation strain gage (and mathematical elimination of the error), or the need to fabricate a non-stressed mounting point for the temperature compensation gage.

Figure 11:
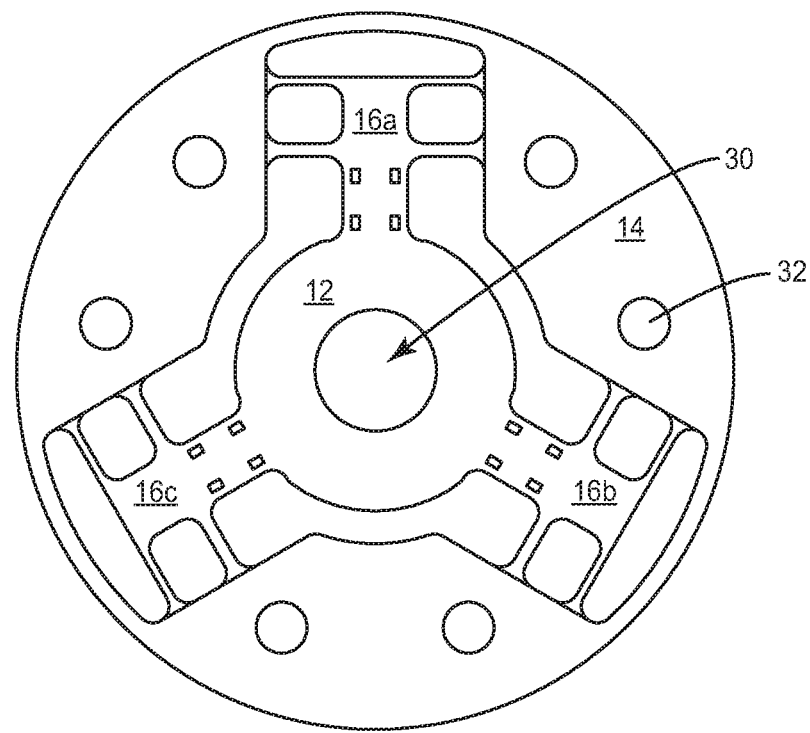
FIG. 11 is a plan view of a force/torque sensor with two pair of strain gages affixed to the top surface only of each beam.

The primary disadvantage of half bridge circuit topology embodiments described above is the need to mount strain gages on both the top and bottom surface of each beam 16. FIG. 11 depicts a force/torque sensor 10 in which two pair of strain gages are affixed to the top surface only of each beam 16. As in the single pair embodiments, the two pair strain gages are each affixed to the top surface only of the beam 16, on either side of, and spaced apart from, the neutral axis of the beam 16. In some embodiments, a strain-concentrating hole may be formed through the beam 16, between each pair of strain gages.

Figure 12:
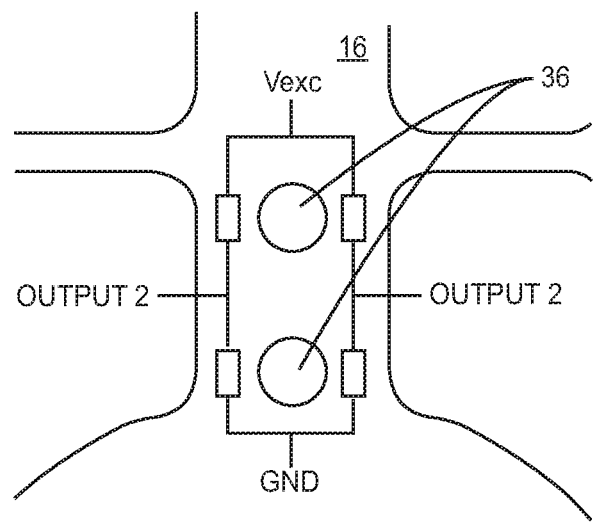
FIG. 12 is an enlarged view of one beam of the force/torque sensor of FIG. 9, with an overlaid functional circuit schematic depicting a half bridge topology.

In this embodiment, multiple flexures 17 on each beam 16 prevent significant compressive and tensile beam loading, while largely preventing rotation at the free end of the beams 16. This causes the beams 16 to deform in shear under all loading conditions. Thus, the gages, when electrically connected as shown in FIG. 12, always are strained by approximately equal amounts but in the opposite direction (tension/compression) under all loading conditions. The mechanical design of this embodiment presents some added complexity, but can be manufactured by the same process and tools as discussed with respect to the embodiment of FIGS. 4A-4G, and it additionally results in an increase in overall stiffness.

Advantages

Embodiments of the present invention present numerous advantages over prior art force/torque sensors. By locating strain gages 1-6 in pairs straddling, and spaced apart from, the neutral axis on only the top surface of each beam 16, the fabrication of a compact force/torque sensor 10 is possible. In one embodiment, the sensor 10 may be fabricated from a single piece of metal, using only conventional milling operations. The ease of access to the strain gages 1-6 enables the use of automated wire bonding to a PCB, or automated pick-and-place on a flexible substrate—in both cases, eliminating manual placement and/or wiring. All embodiments exhibit zero-sum coefficients in five of six force/torque axes, enabling the mathematical elimination of common-mode signals, such as those induced by temperature changes. Temperature compensation may also be applied in quarter bridge topology embodiments by placement of a temperature compensating strain gage on a non-stressed member of the sensor 10. In half bridge topology embodiments, by placing an additional pair of strain gages on the bottom surface of each beam 16, common-mode signals are electrically eliminated in the five of six zero-sum force/torque axes. In one embodiment, the non-zero-sum axis may be changed by reversing the excitation polarity, thus fully resolving all six axes with electrical temperature drift elimination. One embodiment allows a half bridge topology while retaining the advantages of top-surface only strain gage mounting.

Embodiments of the present invention have been depicted and described as having three beams 16a, 16b, 16c. While three instrumented beams 16 is the minimum number required to resolve 6-axis force/torque loading, in some cases more beams 16 may be desirable. More beams may, for example, add stiffness to a sensor 10, and/or may provide redundancy in the event the instrumentation on a beam fails in the field. In certain applications, where full 6-axis force/torque resolution is not required, a sensor 10 may employ two, or even one beam 16.

For convenience and to provide a consistent context in which to discuss the principles and operation of force/torque sensors, the beams connecting a TAP and MAP, both in the prior art and in embodiments of the present invention, are described herein in terms of having four surfaces—that is, a square or rectangular cross-section. While this is a common and economical configuration, nothing in the present disclosure limits embodiments of the invention to four-surface beams. Those of skill in the art will readily appreciate that a beam may be formed with any polygonal cross-section (e.g., triangular, octagonal, etc.), or with an arcuate cross-section (e.g., circular, elliptical, ovoid, etc.). As used herein, the terms "one surface," top/bottom/side/left/right surface, and the like, as applied to a beam with other than a square or rectangular cross-section, mean the extent of the beam that is viewed or accessed from one of four orthogonal directions, as defined by the force/torque reference axes. Thus, for example, a pair of strain gages affixed to a beam having a circular cross-section would be considered as being on the same, top, "side" if both gages were within approximately +/−45° of the central axis projected to the surface in the z-axis direction to establish a 0° reference line longitudinally along the beam. Those of skill in the art may readily apply the teachings of the present invention to other beam shapes.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A force/torque sensor comprising:
   a Tool Adapter Plate (TAP) operative to be connected to a first object:
   a Mounting Adapter Plate (MAP) operative to be connected to a second object;
   a one or more deformable beams connecting the TAP to the MAP, each deformable beam having a plurality of sides, and each side having a neutral axis, undergoing no strain, at the transition of tensile and compressive forces to either side of the neutral axis;
   a first pair of strain gages affixed to only a first side of each beam, the strain gages on opposite sides of, and spaced apart from, the neutral axis of the beam on the first side and operative to transduce tensile and compressive forces on the surface of the first side of the beam, caused by deformation of the beam, into electrical signals; and
   a measurement circuit operative to measure, in response to electrical signals from all strain gages, the direction and magnitude of force and torque between the first and second objects.

2. The sensor of claim 1 wherein
   the first object is a robotic tool or a mechanical coupling to a robotic tool; and
   the second object is a robotic arm or a mechanical coupling to a robotic arm.

3. The sensor of claim 1 further comprising a strain-concentrating hole through each beam between the strain gages on the first side of the beam.

4. The sensor of claim 1 wherein the pair of strain gages affixed to a beam are electrically connected in quarter-bridge topology with two fixed resistors.

5. The sensor of claim 1 further comprising a circuit board containing the measurement circuit, and wherein electrical connections are wire bonded from pads on the circuit board to the strain gages.

6. The sensor of claim 1 further comprising a flexible circuit substrate, wherein the pair strain gages are surface-mounted on the flexible circuit substrate, and wherein at least a portion of the flexible circuit substrate containing the strain gages extends over, and is adhered to, a beam.

7. The sensor of claim 1 wherein the TAP, MAP, and beams are all machined from a single piece of metal stock and form an integral unit.

8. The sensor of claim 1, further comprising a non-stressed member connected to one of the TAP and the MAP but not the other, which does not deform in response to a force or torque between the first and second objects, and further comprising a temperature-compensating strain gage affixed to the non-stressed member.

9. The sensor of claim 1, wherein the output of each strain gage has a positive or negative polarity, and wherein the sum of all outputs of all strain gages is zero for at least five of six force/torque axes selected from the group Fx, Fy, Fz, Tx, Ty, Tz.

10. The sensor of claim 9 wherein the sum of all outputs of all strain gages is not zero for the Fz axis.

11. The sensor of claim 10 further comprising a strain-concentrating hole through the beam between the strain gages of each pair.

12. The sensor of claim 1 further comprising a second pair of strain gages affixed to a second side that is opposite to the first side of each beam, the second pair of strain gages on opposite sides of, and spaced apart from, the neutral axis of the beam on the second side and operative to transduce tensile and compressive forces on the surface of the second side of the beam, caused by deformation of the beam, into electrical signals, and wherein the first and second pair of strain gages on each beam are connected in a half bridge topology.

13. The sensor of claim 12 wherein the sum of all outputs of all strain gages is zero for at least five of six force/torque axes selected from the group Fx, Fy, Fz, Tx, Ty, Tz, and wherein the one force/torque axis for which the strain gage outputs do not sum to zero is changed by reversing the excitation polarity of one of the strain gages on each beam.

14. The sensor of claim 1 further comprising a second pair of strain gages affixed to the first side of each beam, the second pair of strain gages on opposite sides of, and spaced apart from, the neutral axis of the beam on the first side and operative to transduce tensile and compressive forces on the surface of the beam, caused by deformation of the beam, into electrical signals, and wherein the first and second pair of strain gages on each beam are connected in a half bridge topology.

* * * * *